(12) United States Patent
Khopade et al.

(10) Patent No.: US 11,241,443 B2
(45) Date of Patent: Feb. 8, 2022

(54) OPHTHALMIC SOLUTION OF BIMATOPROST

(71) Applicant: SUN PHARMA ADVANCED RESEARCH COMPANY LIMITED, Mumbai (IN)

(72) Inventors: Ajay Jaysingh Khopade, Baroda (IN); Arindam Halder, Baroda (IN)

(73) Assignee: SUN PHARMA ADVANCED RESEARCH COMPANY LTD., Mumbai (IN)

( * ) Notice: Subject to any disclaimer, the term of this patent is extended or adjusted under 35 U.S.C. 154(b) by 8 days.

(21) Appl. No.: 16/476,138

(22) PCT Filed: Apr. 7, 2018

(86) PCT No.: PCT/IN2018/050201
§ 371 (c)(1),
(2) Date: Jul. 5, 2019

(87) PCT Pub. No.: WO2018/185788
PCT Pub. Date: Oct. 11, 2018

(65) Prior Publication Data
US 2020/0016169 A1 Jan. 16, 2020

(30) Foreign Application Priority Data
Apr. 7, 2017 (IN) .............................. 201721012499

(51) Int. Cl.
| | | |
|---|---|---|
| *A61K 31/5575* | (2006.01) | |
| *A61K 47/18* | (2017.01) | |
| *A61K 9/00* | (2006.01) | |
| *A61K 9/08* | (2006.01) | |

(52) U.S. Cl.
CPC ........ *A61K 31/5575* (2013.01); *A61K 9/0048* (2013.01); *A61K 9/08* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 2002/0103255 A1* | 8/2002 | Hellberg | A61K 31/215 514/530 |
| 2011/0251285 A1 | 10/2011 | Tien et al. | |
| 2013/0281420 A1* | 10/2013 | Taraporewala | A61K 31/56 514/182 |
| 2014/0121209 A1* | 5/2014 | Pujara | A61K 47/02 514/236.2 |

FOREIGN PATENT DOCUMENTS

| | | | | |
|---|---|---|---|---|
| EP | 1792972 A1 | 6/2007 | | |
| WO | 0024425 A1 | 5/2000 | | |
| WO | 2016016908 A1 | 2/2016 | | |
| WO | WO-2016016908 A1 * | 2/2016 | ............. | A61P 27/02 |

OTHER PUBLICATIONS www.uwsp.edu, Types of Solutions, Feb. 1, 2001, printed from http://www.uwsp.edu/chemistry/tzamis/chem106pdfs/solutionexamples.pdf, Google date sheet included, 2 pages.*
International Application No. PCT/IN2018/050201, International Search Report dated Sep. 11, 2018, 6 pages.

* cited by examiner

*Primary Examiner* — Gigi G Huang
(74) *Attorney, Agent, or Firm* — Sughrue Mion, PLLC

(57) ABSTRACT

The present invention relates to an ophthalmic solution comprising
 (i) bimatoprost or its pharmaceutically acceptable salt in an amount ranging from about 0.005% to 0.015% weight by volume;
 (ii) a biguanide compound in an amount ranging from about 0.003% to 0.05% weight by volume;
 (iii) an acylated amino acid in an amount ranging from about 0.01% to 0.1% weight by volume;
 (iv) pharmaceutically acceptable excipients and
 (v) purified water.

1 Claim, 1 Drawing Sheet

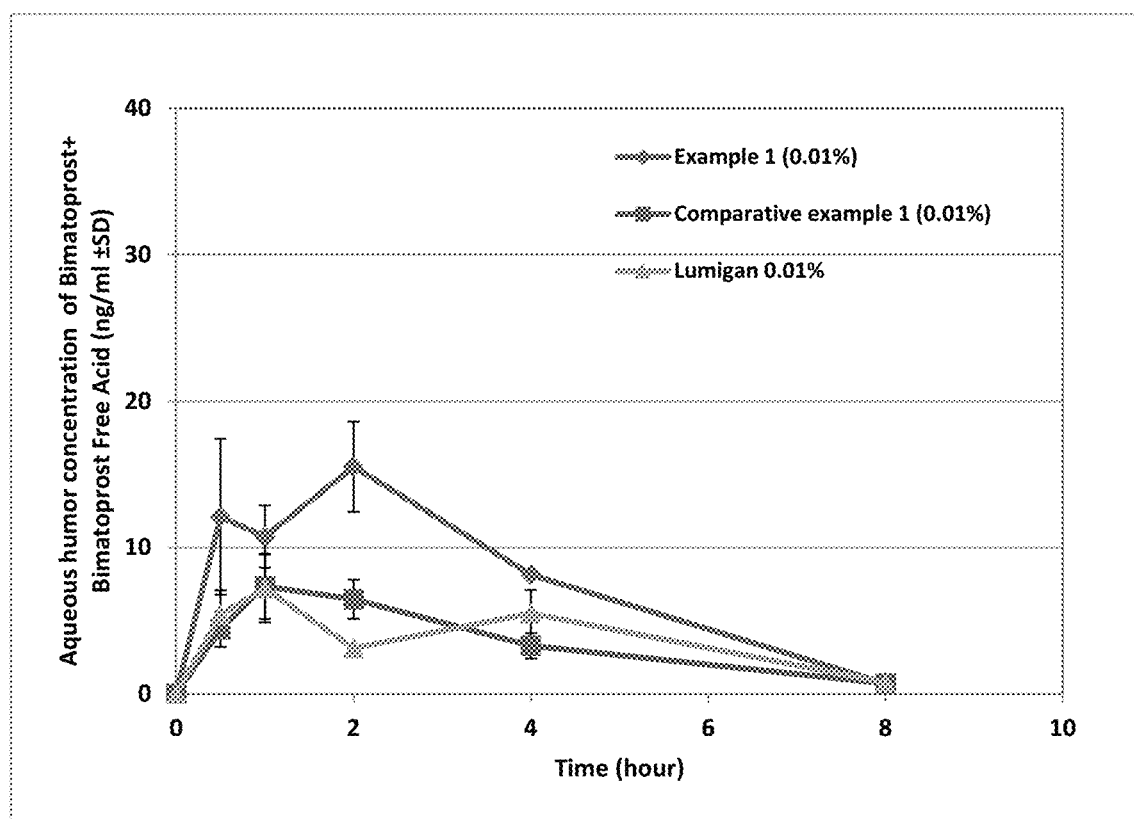

OPHTHALMIC SOLUTION OF BIMATOPROST

FIELD OF THE INVENTION

The present invention relates to a novel ophthalmic solution of bimatoprost or its pharmaceutically acceptable salts.

BACKGROUND OF THE INVENTION

Bimatoprost is available at 0.03% w/v concentration with 0.05 mg/ml of benzalkonium chloride, under the brand name of Latisse® by Allergan. This product is used to treat hypotrichosis of the eyelashes by increasing their growth including length, thickness and darkness. The solution contained 0.05 mg/ml of benzalkonium chloride as preservative. Later, ophthalmic solution of bimatoprost at 0.03% w/v concentration and 0.05 mg/ml of benzalkonium chloride, for reducing elevated intra-ocular pressure in patients with open angle glaucoma or ocular hypertension was made available by Allergan, under the brand name Lumigan® 0.03%. Allergan subsequently improved this by reducing the bimatoprost concentration to 0.01% w/v (Lumigan® 0.01%), but contained very high concentration of benzalkonium chloride i.e. 0.2 mg/ml which is as high as four times the concentration present in Latisse® and Lumigan® 0.03%.

The present inventors have found an ophthalmic solution of bimatoprost that show high ocular bioavailability without use of benzalkonium chloride. In fact the present inventors have found ophthalmic solutions that have improved ocular bioavailability as compared to the marketed preparation that uses benzalkonium chloride 0.2 mg/ml as a penetration enhancer and preservative. The inventors obtained the result with the use of acylated amino acid in combination with a biguanide compound preservative.

SUMMARY OF THE INVENTION

The present invention provides an ophthalmic solution comprising—
(i) bimatoprost or its pharmaceutically acceptable salt in an amount ranging from about 0.005% to 0.015% weight by volume;
(ii) a biguanide compound present in an amount ranging from about 0.003% to 0.05% weight by volume;
(iii) an acylated amino acid present in an amount ranging from about 0.01% to 0.1% weight by volume;
(iv) pharmaceutically acceptable excipients and
(v) purified water;

BRIEF DESCRIPTION OF FIGURE

FIG. 1: Graph showing aqueous humor concentration of bimatoprost+bimatoprost free acid versus time (in hour) observed for ophthalmic solution of example 1 ( ); ophthalmic solution of comparative example 1 ( ) and ophthalmic solution of reference product Lumigan, 0.01% ( ), as per the study described in Example 7.

DETAILED DESCRIPTION OF THE INVENTION

The term 'ocular bioavailability' as used herein refers to the rate and extent of absorption of the drug in eye upon instillation of the ophthalmic solution into the eye.

The ophthalmic solution according to the present invention is a clear aqueous solution and is not an emulsion, suspension, dispersion, gel, or nanodispersion. All the components of the ophthalmic solution are soluble and form a clear solution in purified water.

The phrase 'preservative efficacy test' refers to a test laid down by regulatory authorities to validate the preservative efficacy or sterility of the pharmaceutical preparations containing a preservative. Typically, preservatives are added in sterile pharmaceutical preparations that are meant to be used multiple times and not for single use. Such preparations are generally ophthalmic preparations, subcutaneous or intramuscular injections stored in multiple dose containers. In such preparations, an antimicrobial agent or preservative is included to inhibit the growth of the micro-organisms. The Pharmacopoeias of various countries provide procedure and criteria to check whether the preparations pass the preservative efficacy test. For instance, according to United States Pharmacopoeia, the requirements for antimicrobial effectiveness are met if:

1) Log reduction in bacterial count at day 7 is not less than 1.0 log reduction from the initial calculated count; the "log reduction in bacteria" at day 14 is not less than 3.0 log reduction from the initial count; and there is no increase in bacterial count at day 28 compared to the previous reading at day 14.
2) There is no increase in counts of yeasts and moulds from the initial calculated counts at 7, 14 and 28 days.

According to European Pharmacopoeia, the sterile preparations like ophthalmic solution complies with requirement (criteria B) if "log reduction in bacteria" at 24 hour is not less than 1.0 log reduction; the "log reduction in bacteria" is not less than 3 log reduction when tested at day 7; the "log reduction in fungi" is not less than 1 log reduction when tested at day 14 and when tested at 28 days there is no increase in the number of viable micro-organisms (bacteria or fungi) compared to the previous reading.

The ophthalmic solution according to the present invention comprises bimatoprost as a sole therapeutically active ingredient. It is present in an amount ranging from about 0.005% to 0.015% weight by volume, such as 0.005, 0.006, 0.007, 0.008, 0.009, 0.01, 0.011, 0.012, 0.013, 0.014 or 0.015% w/v. The concentration (% w/v or % weight by volume) of bimatoprost as expressed herein refers to concentration of bimatoprost base. In one preferred embodiment, bimatoprost is present in the ophthalmic solution in an amount of 0.01% w/v.

It was surprisingly found out that the ophthalmic solution of the present invention showed improved ocular bioavailability of bimatoprost compared to the marketed preparation of 0.01% weight by volume of bimatoprost (Lumigan® 0.01% w/v) containing very high concentration of benzalkonium chloride (0.2 mg/ml). It was indeed unexpected to achieve improvement in the ocular bioavailability using very small amount of an acylated amino acid along with a biguanide compound which is a preservative. Thus, the present invention advantageously avoided use of benzalkonium chloride and yet achieved improved ocular bioavailability using a novel ophthalmic solution of bimatoprost. Benzalkonium chloride is reported to cause tear film instability, loss of goblet cells, conjunctival squamous metaplasia and apoptosis, disruption of the corneal epithelium barrier, and damage to deeper ocular tissues (Baudocin et al, Prog Retin Eye Res, 2010; 29(4): 312-334). Thus, the present invention solved the problem by discovering a novel ophthalmic solution that is free of benzalkonium chloride with the help of acylated amino acid which is a penetration enhancer and biguanide compound which is a preservative.

The acylated amino acids according to the present invention are N-acyl fatty acid derivatives of natural amino acids. These are generally anionic in nature and are soluble in water. The acylated amino acid used in the ophthalmic solution is selected from a group consisting of but not limited to acyl sarcosines or sarcosinates, acyl glutamates, acyl glycinates, acyl aspartates, acyl taurates, acyl malonates or acyl amino-malonates, their salts or mixtures thereof. Generally the salts include sodium salt, potassium salt, ammonium salt, amine salt, triethanolamine salt and the like.

The acyl sarcosines and their salts are represented by formula I given below:

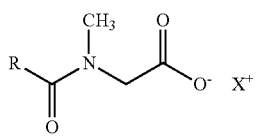

Formula I wherein R is a fatty acid group having $C_4$-$C_{21}$ carbon atoms

X represents salt for example sodium salt, potassium salt, ammonium salt, amine salt, tri-ethanol amine salt and the like.

Non-limiting examples of acyl sarcosines include, but are not limited to, N-lauroyl sarcosine, N-oleoyl sarcosine, N-stearoyl sarcosine, N-myristoyl sarcosine, N-cocoyl sarcosine or their salts such as N-lauroyl sarcosine sodium or sodium N-lauroyl sarcosinate, N-lauroyl sarcosine potassium or potassium N-lauroyl sarcosinate, sodium N-oleoyl sarcosinate, sodium N-stearoyl sarcosinate, sodium N-myristoyl sarcosinate, sodium N-cocoyl sarcosinate, ammonium cocoyl sarcosinate, ammonium lauroyl sarcosinate and the like or mixtures thereof.

Non-limiting examples of acyl glutamates include but are not limited to N-lauroyl glutamate, N-oleoyl glutamate, N-stearoyl glutamate, N-myristoyl glutamate or salts thereof such as for example mono-sodium N-lauroyl glutamate; potassium N-lauroyl glutamate and the like or mixtures thereof.

Non-limiting examples of N-acyl glycinates include but are not limited to N-lauroyl glycinate, N-oleoyl glycinate, N-stearoyl glycinate, N-myristoyl glycinate or salts thereof. Non-limiting examples of N-acyl aspartate include but are not limited to N-lauroyl apartate, N-oleoyl apartate, N-stearoyl aspartate, N-myristoyl aspartate or salts thereof. Non-limiting examples of N-acyl taurates include but are not limited to N-lauroyl taurate, N-oleoyl taurate, N-stearoyl taurate, N-myristoyl taurate, N-methyl acyl taurates or salts thereof. Non-limiting examples of acyl aminomalonates include but are not limited to N-lauroyl aminomalonate, N-oleoyl aminomalonate, N-stearoyl aminomalonate, N-myristoyl aminomalonate or salts thereof.

The acylated amino acid is present in an amount ranging from about 0.01% to 0.1% w/v, such as for example 0.01, 0.02, 0.03, 0.04, 0.05, 0.06, 0.07, 0.08, 0.09 or 0.1% w/v, preferably in an amount ranging from 0.03% to 0.06% w/v. In preferred embodiments, the acylated amino acid is a sarcosine compound i.e. N-acyl sarcosine or its salt. Preferably it is N-lauroyl sarcosine or its salt. N-lauroyl sarcosine or its salt is present in an amount ranging from about 0.01% to 0.1% w/v, preferably from about 0.01% to 0.06% w/v. In particularly preferred embodiment, the acylated amino acid is sodium salt of N-lauroyl sarcosine, i.e. N-lauroyl sarcosine sodium or sodium N-lauroyl sarcosinate, which is represented by compound of formula II below:

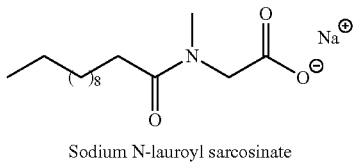

Formula II

Sodium N-lauroyl sarcosinate

It is present in the ophthalmic solution in an amount ranging from about 0.01% to 0.1% w/v, preferably from about 0.03 to 0.06% w/v, such as for example 0.03, 0.035, 0.04, 0.045, 0.05, 0.055, 0.06% w/v. In another preferred embodiment, the acylated amino acid is sodium salt of N-lauroyl glutamate, i.e. mono sodium N-lauroyl glutamate and it is present in the ophthalmic solution in an amount ranging from about 0.01% to 0.1% w/v, preferably from about 0.03 to 0.06% w/v.

The biguanide compounds that are used as a preservative in the ophthalmic solution according to the present invention have a markush chemical structure represented by formula III below:

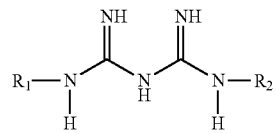

Formula III wherein R1 and R2 can be substituted or un-substituted aliphatic, aromatic or heterocyclic organic group/s, further wherein R1 and R2 may be same or different.

In some preferred embodiments, the biguanide compounds according to the present invention are polymeric biguanides such as represented by formula IV below:

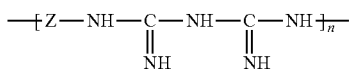

Formula IV wherein Z is an organic group and wherein n varies from 1 to 500, preferably 5 to 20.

Preferably, the biguanide compound may be selected from the group consisting of polyhexamethylene biguanide, alkyl-biguanide, polyoxyalkylene diamine biguanide or their water-soluble salt; 1,1'-hexamethylene-bis-{5-(4-chlorophenyl)-biguanide}; 1,1'-hexamethylene-bis-{5-(2-ethylhexyl) biguanide},1,1'-hexamethylene-bis-{5-(4-fluoro phenyl)-biguanide}; (N,N"-bis(2-ethyl hexyl)-3,12-diimino-2,4,11,13-tetraazatetra decanediimidamine, chlorhexidine or their salts, and the like and mixtures thereof. The salts of biguanide compounds include but are not limited to hydrochloride, gluconate, digluconate, borate, acetate, sulphonate, tartrate, citrate. The biguanide compound is present in an amount ranging from about 0.003 to 0.05% w/v such as for example 0.003, 0.004, 0.005, 0.006, 0.007, 0.008, 0.009, 0.01, 0.02, 0.03, 0.04 or 0.05% w/v.

In a particularly preferred embodiment, the biguanide compound is polyhexamethylene biguanide or its salt. Polyhexamethylene biguanide is represented by compound of formula V below:

Formula V

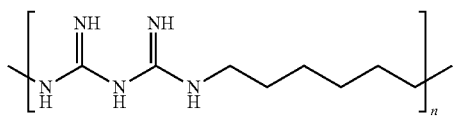

Polyhexamethylene biguanide is a polymeric biguanide (wherein Z is hexamethylene group) having a weighted average number (n) of 12 (range 2 to 40) repeating hexamethylene biguanide units. It is also known as polyhexanide or PHMB or polyaminopropyl biguanide or PAPB and its IUPAC name is homopolymer of N-(3-Aminopropyl)-Imidodicarbonimidic diamide. Suitable salts of polyhexamethylene biguanide include but are not limited to hydrochloride, gluconate, digluconate, borate, acetate, sulphonate, tartrate, citrate, preferably hydrochloride salt. It is present in the ophthalmic solution in an amount ranging from about 0.003% to 0.05% w/v, such as for example 0.003, 0.004, 0.005, 0.006, 0.007, 0.008, 0.009, 0.01, 0.02, 0.03, 0.04 or 0.05% w/v, preferably in an amount ranging from about 0.003-0.01% w/v, more preferably in an amount ranging from about 0.003-0.005% w/v.

In another preferred embodiment, the biguanide compound is chlorhexidine or its salt represented by compound of formula VI below:

Formula VI

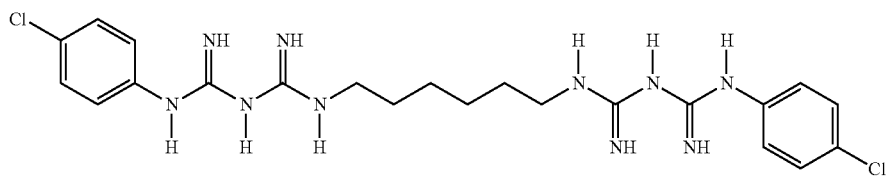

and it is present in an amount ranging from about 0.003% to 0.05% w/v, preferably in an amount ranging from about 0.003-0.01% w/v, more preferably in an amount ranging from about 0.003-0.005% w/v. Preferred salts of chlorhexidine are chlorhexidine digluconate or chlorhexidine diacetate. Apart from the biguanide compound, the ophthalmic solution may additionally contain one or more other preservatives such as boric acid, borates, sorbic acid, potassium sorbate, Polyquad®, stabilized peroxides and perborates, stabilized oxychloro compounds, benzyl alcohol, cetrimide, chlorobutanol, mercurial preservatives like phenylmercuric nitrate, phenylmercuric acetate, thimerosal, phenylethyl alcohol, edetate disodium, parabens (such as methyl, propyl, isopropyl and butyl paraben) and the like and mixtures thereof. It is to be noted that the ophthalmic solution is free of benzalkonium chloride.

The amount of acylated amino acid and biguanide compound used in the ophthalmic solution is in the range in which the ophthalmic solution provides improvement in the ocular bioavailability while retaining sterility throughout the shelf life of the solution. The present inventors had encountered a problem of loss of antimicrobial activity when the biguanide compound, for eg. polyhexamethylene biguanide was used at certain concentrations relative to concentration of acylated amino acid, for eg. N-lauroyl sarcosine. In one of the trials, when polyhexamethylene biguanide was used at a concentration of 0.002% w/v and N-lauroyl sarcosine sodium was used at a concentration of 0.03% w/v (comparative example 2), the ophthalmic solution was found to lose its preservation activity or sterility. The ophthalmic solution was not able to control the bacterial and fungal growth. This problem was encountered while subjecting the ophthalmic solution to preservative effectiveness testing (PET) prescribed by various Pharmacopoeias. These solutions did not comply with requirement in that "log reduction in bacteria" was less than 1.0 log reduction when observed at 24 hour and/or the "log reduction in bacteria" was less than 3 log reduction when tested at day 7 and/or the "log reduction in fungi" was less than 1 log reduction when tested at day 14 and/or an increase in the number of viable micro-organisms (bacteria or fungi) was observed at day 28 compared to the previous reading. On the other hand, when ophthalmic solution contained 0.001% w/v of polyhexamethylene biguanide but without acylated amino acid, although the ophthalmic solution complied with the sterility requirement and passed the PET, this solution did not show any improvement in ocular bioavailability. Without wishing to be bound by any theory, the inventors believe that when acylated amino acid like N-lauroyl sarcosinate is present beyond a certain concentration relative to the concentration of biguanide compound, there seems to be an interaction with the biguanide compound, for example polyhexamethylene biguanide. This may affect the preservative activity of polyhexamethylene, a biguanide compound. Generally, it was found that when the concentration of acylated amino acid is more than 12 times the concentration of biguanide compound, there was loss in the preservation/sterility of the ophthlamic solution on storage. Thus, based on the experiments of polyhexamethylene biguanide compound and N-lauroyl sarcosinate sodium, it is generally noted that the weight ratio of acylated amino acid to biguanide compound should be not more than 12:1.

In contrast, the ophthalmic solution of the present invention comprising bimatoprost in an amount ranging from about 0.005 to 0.015% weight by volume, an acylated amino acid, particularly N-lauroyl sarcosinate sodium present in an amount ranging from about 0.01% to 0.1% weight by volume; a biguanide compound particularly polyhexamethylene biguanide present in an amount ranging from about 0.003% to 0.05% weight by volume, pharmaceutically acceptable excipients and purified water when subjected to PET, complied with requirement in that "log reduction in bacteria" was not less than 1.0 log reduction when observed at 24 hour; the "log reduction in bacteria" was not less than 3 log reduction when tested at day 7; the "log reduction in fungi" was not less than 1 log reduction when tested at day 14 and when tested at 28 days there was no increase in the number of viable micro-organisms (bacteria or fungi) compared to the previous reading.

Preferably, the ophthalmic solution of the present invention comprising 0.01% weight by volume of bimatoprost base, an acylated amino acid, particularly N-lauroyl sarcosinate sodium present in an amount ranging from about 0.01% to 0.06% weight by volume; a biguanide compound particularly polyhexamethylene biguanide present in an amount ranging from about 0.003% to 0.01% weight by volume, pharmaceutically acceptable excipients comprising additional preservative like boric acid present in an amount of 0.5% to 2.0% w/v, pH adjusting agents such as arginine or tromethamine, cosolvents like polyethylene glycol, viscosity modifying agents like hydroxypropyl methyl cellulose and polyvinylpyrrolidone and the like and mixtures thereof and purified water when subjected to the PET, complied with requirement in that "log reduction in bacteria" was not less than 1.0 log reduction when observed at 24 hour; the "log reduction in bacteria" was not less than 3 log reduction when tested at day 7; the "log reduction in fungi" was not less than 1 log reduction when tested at day 14 and when tested at 28 days there was no increase in the number of viable micro-organisms (bacteria or fungi) compared to the previous reading. Thus, the present inventors discovered a composition of an ophthalmic solution that not only provided improved ocular bioavailability, but also was capable of maintaining sterility throughout the shelf life.

Based on the various findings, it could be said that the weight ratio of acylated amino acid to biguanide compound should be not more than 12:1, preferably the weight ratio is in the range of 6:1 to 12:1, particularly when the acylated amino acid is N-lauroyl sarcosinate sodium and the biguanide compound is polyhexamethylene biguanide. When the weight ratio of acylated amino acid to biguanide compound is more than 12:1, such as 15:1 (comparative example 2) or 60:1 (comparative example 3), the ophthalmic solution did not comply with the criteria of the prescribed PET test.

The ophthalmic solution according to the present invention comprises other pharmaceutically acceptable excipients, which may be selected from but not limited to viscosity modifying agent, pH adjusting agent, buffer, osmotic agent, chelating agent, co-solvent, preservatives other than benzalkonium chloride. It is to be noted that the ophthalmic solution of the present invention does not include surfactants other than acylated amino acids. Such other surfactants include, polysorbate 80, polyoxyl-80-hydroxystearate, macrogol glycerol hydroxystearate 40. Further, the ophthalmic solution is free of oils or oily excipients such as for example mineral oil, castor oil, hydrogenated castor oil and the like. The ophthalmic solution is also free of stabilizers like hyaluronic acid. The ophthalmic solution is also free of solubilizers like polyvinyl alcohol, ethyl alcohol, methyl alcohol. The ophthalmic solution according to the present invention is not a gel and is not intended to gel upon topical instillation/application into the eye. The ophthalmic solution in preferred embodiments is thus free of gel forming agents like polyacrylates and carbomers.

In one or more embodiments, the ophthalmic solution of bimatoprost according to the present invention consists essentially of bimatoprost in an amount ranging from about 0.005 to 0.015% weight by volume; an acylated amino acid, particularly N-lauroyl sarcosinate sodium, in an amount ranging from about 0.01% to 0.1% weight by volume; a biguanide compound particularly polyhexamethylene biguanide, in an amount ranging from about 0.003% to 0.05% weight by volume, pharmaceutically acceptable excipients and purified water. The term 'consists essentially' as used herein means that the ophthalmic solution does not make use of or is free of benzalkonium chloride. The term further means that the ophthalmic solution does not make use of or is free of surfactants other than acylated amino acids, such as polysorbate 80, polyoxyl-80-hydroxystearate, macrogol glycerol hydroxystearate 40; is free of oils or oily excipients such as for example mineral oil, castor oil, hydrogenated castor oil and the like, is free of stabilizers like hyaluronic acid; is free of solubilizers like polyvinyl alcohol, ethyl alcohol, methanol; and is free of gel forming agents like polyacrylates and carbomers.

The ophthalmic solution of the present invention has a pH in the range of about 6.0 to 8.0, preferably in the range of 6.5 to 7.5 such as for example 6.5, 6.55, 6.6, 6.65, 6.7, 6.75, 6.8, 6.85, 6.9, 6.95, 7.0, 7.05, 7.1, 7.15, 7.2, 7.25, 7.3, 7.35, 7.4, 7.45 or 7.5 or intermediate values thereof. Preferably, the pH of the ophthalmic solution is about 7.0 (7±0.2). The pH adjusting agents and/or buffering agent that are used in the ophthalmic solution according to the present invention are selected from, but not limited to, L-arginine, tromethamine, acetic acid, sodium acetate, tartaric acid, sodium tartrate, citric acid, sodium citrate, lactic acid, sodium lactate, hydrochloric acid, sodium hydroxide or mixtures thereof. In preferred embodiments, the pH adjusting and/or buffering agent agent is arginine or tromethamine and it is used in an amount ranging from about 0.01% to 0.5% weight by volume, preferably in an amount of 0.05% to 0.15% w/v.

The viscosity modifying agent that can be used according to the present invention are selected from cellulose based polymers like hydroxypropyl methylcellulose, hydroxyethyl cellulose, hydroxypropyl cellulose, methylcellulose, carboxymethylcellulose, vinyl pyrrolidone polymers like polyvinyl pyrrolidones, or other agents like hydroxyethyl starch or dextran and the like or mixtures thereof. In one preferred embodiment, viscosity modifying agent includes a mixture of hydroxypropyl methyl cellulose and polyvinyl pyrrolidone. Various grades of hydroxypropyl methyl cellulose are available that may be used in the ophthalmic solution. In preferred embodiment, the ophthalmic solution comprises hydroxypropyl methyl cellulose having a viscosity in the range of 2700 cps to 5600 cps at 20° C. for a 2% w/v aqueous solution. It is present at a concentration varying from 0.05% to 0.5% w/v, such as for example 0.05, 0.06, 0.07, 0.08, 0.09, 0.10, 0.15, 0.20, 0.25, 0.30, 0.35, 0.40, 0.45, 0.5% w/v. In particularly preferred embodiment, the ophthalmic solution comprises hydroxypropyl methyl cellulose, grade E4M Premium 2910 that has a viscosity of about 4000 cps at 20° C. for a 2% w/v aqueous solution. It may be used in the ophthalmic solution at a concentration varying from 0.05 to 0.5% w/v, preferably 0.2 to 0.5% w/v. Various grades of polyvinylpyrrolidone are available that may be used in the ophthalmic solution such as PVP K-12, PVP K-15, PVP K-25, PVP K-30, PVP K-60, PVP K-90, and the like. In preferred embodiment, the ophthalmic solution comprises polyvinylpyrrolidone having a viscosity in the range of 300 cps to 700 cps at 20° C. of a 10% w/v aqueous solution. It is present at a concentration varying from 0.05 to 2.0% w/v, such as for example 0.05, 0.06, 0.07, 0.08, 0.09, 0.10, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0% w/v, preferably from about 1.0% to 2.0% w/v.

The viscosity of the aqueous ophthalmic solution according to the present invention ranges from about 5 cps to 75 cps, more preferably from 5 cps to 30 cps such as for example 6, 7, 8, 9, 10, 11, 12, 13, 14, 15, 16, 17, 18, 19, 20, 21, 22, 23, 24, 25, 26, 27, 28, 29 or 30 cps or intermediate values thereof.

The osmotic/tonicity adjusting agents may be selected from propylene glycol, glycerol, sodium chloride, potassium chloride, sodium bromide, calcium chloride, mannitol, sorbitol, dextrose, sucrose, mannose and the like and mixtures thereof. The osmotic agent is used in an amount to maintain the solution's osmolality in the range of 250 to 375 mOsm/ kg, preferably 270-350 mOsm/kg, such as for example 275, 280, 285, 290, 295, 300, 305, 310, 315, 320, 325, 330, 335, 340 or 345 mOsm/kg.

The co-solvent that may be used according to the present invention is selected from propylene glycol, polyethylene glycol, glycerine, glycerol and the like or mixtures thereof. In one preferred embodiment, the co-solvent is polyethylene glycol 400 and it is present in an amount ranging from 1.0% to 5.0% w/v, preferably 2.5 to 4.0% w/v, more preferably, 3.0 to 3.5% w/v.

The ophthalmic solution may contain one or more chelating agents such as edetate disodium, ethylenediamine tetracetic acid, edetic acid, disodium edetate dihydrate, diethylenetriamine pentaacetic acid and the like. A preferred chelating agent is ethylenediamine tertaacetic acid or disodium edetate.

The aqueous ophthalmic solution according to the present invention is clear and free from particles, crystals or precipitates. The ophthalmic solution show percentage transmission greater than 95%, more preferably greater than 98%, more preferably greater than 99%. The ophthalmic solution remains physically and chemically stable upon storage at temperatures between 2° C. to 30° C. for a period of 6 months or more. Upon storage there occurs no substantial change in % assay of bimatoprost and it remains within the desired limit of 95-105% w/v. The level of related substances, i.e. known, unknown and total impurities also remains within the specified limits upon storage.

In preferred embodiments, the ophthalmic solution of the present invention comprises 0.01% weight by volume of bimatoprost base, an acylated amino acid, particularly N-lauroyl sarcosinate sodium present in an amount ranging from about 0.01% to 0.06% weight by volume; a biguanide compound particularly polyhexamethylene biguanide present in an amount ranging from about 0.003% to 0.01% weight by volume, pharmaceutically acceptable excipients such as boric acid present in an amount of 0.5% to 2% by weight, pH adjusting agents such as arginine or tromethamine, cosolvents such as polyethylene glycol, viscosity modifying agents such as hydroxypropyl methyl cellulose and polyvinylpyrrolidone and purified water. This solution when subjected to PET, complied with requirement in that "log reduction in bacteria" was not less than 1.0 log reduction when observed at 24 hour; the "log reduction in bacteria" was not less than 3.0 log reduction when tested at day 7; the "log reduction in fungi" was not less than 1.0 log reduction when tested at day 14 and when tested at 28 days there was no increase in the number of viable microorganisms (bacteria or fungi) compared to the previous reading. Thus, the present inventors discovered a composition of an ophthalmic solution that not only provided improved ocular bioavailability, but also was capable of maintaining sterility throughout the shelf life.

In one particular embodiment, the ophthalmic solution comprising 0.01% w/v of bimatoprost, polyhexamethylene biguanide and N-lauroyl sarcosine sodium, boric acid, arginine, polyethylene glycol, hydroxypropyl methyl cellulose and polyvinylpyrrolidone, was subjected to bioavailability study by topically administering the ophthalmic solution once a day, in rabbit's eyes. The results are provided in Example 7. The results showed significantly higher extent of absorption of bimatoprost ($AUC_{0-8\ hr}$ of 32.55 h*ng/mL) for this solution as compared to extent of absorption obtained upon administration of marketed solution—Lumigan® 0.01% which contains 0.01% w/v bimatoprost base and benzalkonium chloride 0.02%.

It was found that the improved ocular bioavailability was due to the presence of acylated amino acid such as N-lauroyl sarcosine along with biguanide compound. This is evident from the bioavailability results of the ophthalmic solution of comparative example 1, and Lumigan 0.01%, wherein the extent of absorption ($AUC_{0-8\ hr}$) was lower (26.95 h*ng/mL in case of comparative example 1 and 18.71 h*ng/mL in case of Lumigan 0.01%) compared to the extent of absorption (32.55 h*ng/mL) obtained upon administration of ophthalmic solution of present invention.

It was further observed that the rate of absorption ($C_{max}$) of bimatoprost upon administration of ophthalmic solution of present invention was found to be improved as compared to $C_{max}$ value obtained upon administration of solution of comparative example 1 and Lumigan® 0.01%.

The present invention thus provides an ophthalmic solution with improved ocular bioavailability while overcoming the problem of loss in preservative activity, by selecting the acylated amino acid and the biguanide compound in specific amounts and weight ratios.

The ophthalmic solution according to the present invention comprises
(i) bimatoprost or its pharmaceutically acceptable salt in an amount ranging from about 0.005% to 0.015% weight by volume;
(ii) a biguanide compound in an amount ranging from about 0.003% to 0.05% weight by volume;
(iii) an acylated amino acid in an amount ranging from about 0.01% to 0.1% weight by volume;
(iv) pharmaceutically acceptable excipients and
(v) purified water.

In certain embodiment, the ophthalmic solution according to the present invention consists of bimatoprost in an amount ranging from about 0.005 to 0.015% weight by volume; an acylated amino acid in an amount ranging from about 0.01% to 0.1% weight by volume; a biguanide compound in an amount ranging from about 0.003% to 0.05% weight by volume, one or more additional preservatives, pH adjusting agent, osmotic agent, co-solvent or viscosity modifying agent and purified water.

In one or more preferred embodiments, the ophthalmic solution according to the present invention comprises bimatoprost in an amount of 0.01% weight by volume; N-lauroyl sarcosine sodium in an amount ranging from about 0.01% to 0.1% weight by volume; polyhexamethylene biguanide in an amount ranging from about 0.003% to 0.05% weight by volume, boric acid in an amount ranging from about 0.1% to 2.0% w/v, arginine or tromethamine in an amount ranging from about 0.01% to 0.5% weight by volume, polyethylene glycol in an amount ranging from about 1.0 to 5.0% w/v, hydroxypropyl methyl cellulose in an amount ranging from about 0.05 to 0.5% w/v, polyvinylpyrrolidone in an amount ranging from about 0.05% to 2.0% w/v and purified water, wherein the pH of the solution is in the range of 6.5 to 7.5, osmolality of the solution is in the range of 250-375 mOsm/kg and viscosity of the solution is in the range of 5 to 75 cps.

In particularly preferred embodiment, the ophthalmic solution according to the present invention consists of bimatoprost in an amount of 0.01% weight by volume; N-lauroyl sarcosine sodium in an amount ranging from about 0.01% to 0.1% weight by volume; polyhexamethylene biguanide in an amount ranging from about 0.003% to 0.05% weight by volume, boric acid in an amount ranging from 0.1 to 2.0% w/v, arginine or tromethamine in an amount ranging from about 0.01% to 0.5% weight by volume, osmotic agent in an amount to adjust osmolality in the range of 250-375 mOsm/kg, polyethylene glycol in an amount ranging from about 1.0 to 5.0% w/v, hydroxypropyl methyl cellulose in an amount ranging from about 0.05 to 0.5% w/v, polyvinylpyrrolidone in an amount ranging from about 0.05% to 2.0% w/v and purified water.

In most preferred embodiment, the ophthalmic solution according to the present invention comprises bimatoprost in an amount of 0.01% weight by volume; N-lauroyl sarcosine sodium in an amount of 0.03% to 0.06% weight by volume; polyhexamethylene biguanide in an amount of 0.005% weight by volume, boric acid in an amount of 0.5% to 1.5% w/v, arginine or tromethamine in an amount of 0.05% to 0.15% weight by volume, polyethylene glycol 400 in an amount of 2.5 to 4.0% w/v, hydroxypropyl methyl cellulose whose 2% w/v aqueous solution have a viscosity of about 4000 cps at 20° C., present in an amount of 0.2 to 0.5% w/v, polyvinylpyrrolidone (K90) in an amount of 1.0% to 2.0% w/v and purified water. The pH of this solution is about 7.0, osmolality is in the range of 275-350 mOsm/kg and viscosity is in the range of 5 to 75 cps.

In another most preferred embodiment, the ophthalmic solution according to the present invention comprises bimatoprost in an amount of 0.01% weight by volume; N-lauroyl sarcosine sodium in an amount of 0.03% to 0.06% weight by volume; chlorhexidine digluconate in an amount of 0.005% weight by volume, boric acid in an amount of 0.5% to 1.5% w/v, arginine or tromethamine in an amount of 0.05% to 0.15% weight by volume, polyethylene glycol 400 in an amount of 2.5 to 4.0% w/v, hydroxypropyl methyl cellulose whose 2% w/v aqueous solution have a viscosity of about 4000 cps at 20° C., present in an amount of 0.2 to 0.5% w/v, polyvinylpyrrolidone (K90) in an amount of 1.0% to 2.0% w/v and purified water. The pH of this solution is about 7.0, osmolality is in the range of 275-350 mOsm/kg and viscosity is in the range of 5 to 75 cps.

The ophthalmic solution according to the present invention may be prepared by a process comprising the steps of
(1) preparing a solution of acylated amino acid, pH adjusting/buffering agent, preservative other than biguanide, such boric acid in purified water by stirring.
(2) preparing a solution of bimatoprost in another container by dissolving specified amounts of bimatoprost in a co-solvent such as polyethylene glycol
(3) adding the solution of bimatoprost of step 2 to solution of step 1 with stirring;
(4) Adding this mixture of step 3 to an aqueous solution of polymer previously prepared by dissolving specified quantity of viscosity modifying polymers such as HPMC and PVP in water and autoclaving the polymeric mixture at 121° C. for 20 minutes. Alternatively, the aqueous solution of polymer containing specified quantity of viscosity modifying polymers such as HPMC and PVP autoclaved at 121° C. for 20 minutes, after cooling could be added to the mixture of step 3.
(5) Adding specified quantity of biguanide compound such as polyhexamethylene biguanide or chlorhexidine digluconate to the mixture of step 4 with stirring and adjusting the volume using purified water, and
(6) sterilizing by filtering the solution of step (5), through 0.2 micron membrane filter and filling the filtered solution in sterile containers.

The present invention also provides a method of enhancing the ocular bioavailability of bimatoprost, said method comprising once-a-day topical instillation into the eye of a patient, an ophthalmic solution comprising;

(i) bimatoprost or its pharmaceutically acceptable salt in an amount ranging from about 0.005 to 0.015% weight by volume;
(ii) a biguanide compound present in an amount ranging from about 0.003% to 0.05% weight by volume;
(iii) an acylated amino acid present in an amount ranging from about 0.01% to 0.1% weight by volume;
(iv) pharmaceutically acceptable excipients and
(v) purified water;
wherein the solution is free of benzalkonium chloride.

The present invention in another aspect, provides a method for reduction of elevated intraocular pressure in patients with glaucoma or ocular hypertension, said method comprising topically administering once-a-day into the eye of the patient, an ophthalmic solution comprising bimatoprost or its pharmaceutically acceptable salt in an amount ranging from about 0.005% to 0.015% w/v, a combination of a biguanide compound and an acylated amino acid, pharmaceutically acceptable excipient and purified water.

The present invention provides a method for reduction of elevated intraocular pressure in patients with glaucoma or ocular hypertension, said method comprising once a day topical instillation into the eye of the patient, an ophthalmic solution comprising:
(i) bimatoprost or its pharmaceutically acceptable salt in an amount ranging from about 0.005 to 0.015% weight by volume;
(ii) a biguanide compound present in an amount ranging from about 0.003% to 0.05% weight by volume;
(iii) an acylated amino acid present in an amount ranging from about 0.01% to 0.1% weight by volume,
(iv) pharmaceutically acceptable excipients and
(v) purified water,
wherein the solution is free of benzalkonium chloride.

According to one or more embodiments, the present invention provides an ophthalmic solution comprising (i) bimatoprost or its pharmaceutically acceptable salt in an amount ranging from about 0.005 to 0.015% weight by volume; (ii) a biguanide compound present in an amount ranging from about 0.003% to 0.05% weight by volume; (iii) an acylated amino acid present in an amount ranging from about 0.01% to 0.1% weight by volume; (iv) pharmaceutically acceptable excipients and (v) purified water for use in treatment of patients with glaucoma or ocular hypertension by once-a-day topical instillation of the ophthalmic solution into the eye.

According to one or more embodiments, the present invention provides an ophthalmic solution comprising (i) bimatoprost or its pharmaceutically acceptable salt in an amount ranging from about 0.005 to 0.015% weight by volume; (ii) a biguanide compound present in an amount ranging from about 0.003% to 0.05% weight by volume; (iii) an acylated amino acid present in an amount ranging from about 0.01% to 0.1% weight by volume; (iv) pharmaceutically acceptable excipients and (v) purified water for use in enhancing the ocular bioavailability of bimatoprost, by once-a-day topical instillation of the ophthalmic solution into the eye.

In the context of this specification "comprising" is to be interpreted as "including". Aspects of the invention comprising certain elements are also intended to extend to alternative embodiments "consisting" or "consisting essentially" of the relevant elements. Where technically appropriate, embodiments of the invention may be combined.

Embodiments are described herein as comprising certain features/elements. The disclosure also extends to separate embodiments consisting or consisting essentially of said features/elements.

Hereinafter, the invention is more specifically described by way of examples. The examples are not intended to limit the scope of the invention and are merely used as illustrations.

Example 1 to Example 6

The Table 1 below gives details of ophthalmic solution of bimatoprost according to preferred embodiments of the present invention (Example 1 to Example 6)

TABLE 1

Composition details of the ophthalmic solution of bimatoprost

| Ingredients | Example 1 | Example 2 | Example 3 | Example 4 | Example 5 | Example 6 |
|---|---|---|---|---|---|---|
| | % w/v | | | | | |
| Bimatoprost | 0.01 | 0.01 | 0.01 | 0.01 | 0.01 | 0.01 |
| Polyethylene glycol 400 | 3.0 | 3.5 | 3.5 | 3.5 | 3.5 | 3.5 |
| Boric acid | 1.0 | 1.0 | 1.0 | 1.0 | 1.0 | 1.0 |
| L-Arginine | 0.14 | 0.06 | 0.06 | 0.06 | 0.06 | 0.06 |
| Hydroxypropyl methyl cellulose (grade having viscosity of about 4000 cps at 20° C. for a 2% w/v aqueous solution) | 0.5 | 0.3 | 0.3 | 0.3 | 0.3 | 0.3 |
| Polyvinylpyrrolidone (K90) | 2.0 | 1.2 | 1.2 | 1.2 | 1.2 | 1.2 |
| Polyhexamethylene biguanide | — | 0.005 | — | — | — | — |
| Chlorhexidine digluconate | — | — | — | 0.005 | — | — |
| N-lauryl sarcosine sodium | 0.03 | 0.03 | 0.06 | — | 0.03 | — |
| Mono sodium N-lauryl glutamate | — | — | — | 0.03 | — | 0.03 |
| Water | q.s. to 100 ml | | | | | |

Method of Preparation:

Step 1: About one third quantity of water for injection was taken in a container. To this accurately weighed quantities of boric acid, L-arginine and N-lauryl sarcosine sodium (example 1 & 2) or mono sodium N-lauryl glutamate (example 3 & 4) were added. The solution was stirred on a stirrer, such as magnetic stirrer, for about 20 to 30 minutes at about 500 rpm.

Step 2: Accurately weighed quantity of polyethylene glycol 400 was taken in another container and to it accurately weighed quantity of bimatoprost was added and mixed using vortex mixer until bimatoprost gets dissolved completely.

Step 3: Specified quantity of aqueous solution of HPMC polymer and PVP polymer was taken and mixed. The polymer mixture was autoclaved at 121° C. for 20 minutes and then cooled to room temperature.

Step 4: The mixture of step 2 was added to the mixture of step 1 along with stirring on a stirrer. This mixture was then added to the polymer phase of step 3 and stirred well.

Step 5: To the mixture of step 4 specified quantity of polyhexamethylene biguanide (example 1 and 2) or specified quantity of chlorhexidine digluconate (example 3 and 4) was added with stirring. The volume was made upto 100 ml using water for injection. The pH of the resulting solution was measured and was found to be about 7.0.

Step 6: The solution was sterilized by filtration through 0.2 micron membrane filter. The filtered, sterile solution was filled in sterile 5 ml white opaque LDPE bottles.

Example 7

The ophthalmic solutions of example 1 and comparative example 1 were subjected to pharmacokinetic study by using New Zealand Rabbit eye model.

The study involved testing (1) ophthalmic Solution 0.01% w/v of bimatoprost of example 1; (2) ophthalmic solution 0.01% w/v of bimatoprost of comparative example 1 and (3) reference listed marketed drug product—Lumigan® 0.01% of bimatoprost w/v. Each test solution was instilled into a group of 10 rabbits. 28 microlitre (μl) of test solution was instilled using micropipette in cul-de-sac once a day in both the eyes of rabbits and aqueous humor was collected from each eye of animals at 0.5, 1, 2, 4 and 8 hours of single instillation. The samples were analyzed for bimatoprost and bimatoprost acid levels in the aqueous humour by LCMS technique. The concentration versus time profile is presented graphically in FIG. 1. The mean $C_{max}$ in ng/ml and $AUC_{0-8\ hr}$ in h*ng/mL, are summarized below in Table 2

TABLE 2

Results of the pharmacokinetic study:

| Solution tested | $C_{max}$ (ng/mL) Rate of absorption | $AUC_{0-8\ hr}$ (h*ng/mL) Extent of absorption |
|---|---|---|
| Ophthalmic Solution of example 1, (0.01% w/v bimatoprost) | 12.103 | 32.55 |
| Ophthalmic Solution of comparative example 1, (0.01% w/v bimatoprost) | 6.466 | 26.95 |
| Lumigan ®, 0.01% w/v bimatoprost solution (Reference) | 7.20 | 18.709 |

Table 2 shows that ophthalmic solution of example 1 of the present invention (containing 0.01% w/v of bimatoprost, polyhexamethylene biguanide and N-lauroyl sarcosine sodium) showed significantly higher AUC value ($AUC_{0-8\ hr}$ of 32.55 h*ng/mL) as compared to AUC values obtained upon administration of Lumigan 0.01% ($AUC_{0-8\ hr}$ of 18.709 h*ng/mL). The extent of absorption, expressed as $AUC_{0-8\ hr}$ obtained for ophthalmic solution of comparative example 1 ($AUC_{0-8\ hr}$ of 26.95 h*ng/mL), was lower as compared to AUC values obtained upon administration of ophthalmic solution of example 1.

Table 2 further shows that ophthalmic solution of example 1 showed significantly higher $C_{max}$ or rate of absorption as compared to $C_{max}$ value obtained upon administration of solution of comparative example 1 and Lumigan 0.01%.

When the ophthalmic solution contained an acylated amino acid compound like, sodium lauryl sarcosine along with the biguanide like, polyhexamethylene biguanide (ophthalmic solution of example 1 of the present invention) and was tested for ocular bioavailability, it showed significant improvement, in that higher rate and extent of ocular absorption (measured as $C_{max}$ and $AUC_{0-8\ hr}$ values) was achieved as compared to rate and extent of ocular absorption obtained upon Lumigan® 0.01% administration.

Thus, ocular bioavailability was found to be better in case of ophthalmic solution of the present invention (which included a combination of biguanide compound and acylated amino acid, such as sodium lauroyl sarcosine) as compared to the prior art ophthalmic solution, Lumigan® 0.01% which is devoid of a biguanide compound and acylated amino acid but contains 0.02% benzalkonium chloride.

Comparative Examples 1-3

TABLE 3

Composition details of the ophthalmic solution of bimatoprost as per comparative examples 1 to 3

| Ingredients | Comparative Example | | |
|---|---|---|---|
| | I | II | III |
| | % w/v | | |
| Bimatoprost | 0.01 | 0.01 | 0.01 |
| Polyethylene glycol 400 | 3.0 | 3.5 | 3.0 |
| Boric acid | 1.0 | 1.0 | 1.0 |
| L-Arginine | 0.14 | 0.06 | 0.14 |
| Zinc chloride | 0.0025 | — | — |
| Hydroxypropyl methyl cellulose (grade having viscosity of about 4000 cps at 20° C. for a 2% w/v aqueous solution) | 0.5 | 0.3 | 0.5 |
| Polyvinylpyrrolidone (K90) | 2.0 | 1.2 | 2.0 |
| Polyhexamethylene biguanide | 0.005 | 0.002 | 0.001 |
| N-lauryl sarcosine sodium | — | 0.03 | 0.06 |
| Water | q.s. | q.s. | q.s. |

The comparative examples 1-3 were prepared by a process similar to the process of working examples described above, except that in comparative example 1, N-lauroyl sarcosine sodium was not added.

The comparative example 1 is devoid of N-lauroyl sarcosine sodium, an acylated amino acid. The rate and extend of absorption of bimatoprost, i.e. ocular bioavailability of bimatoprost observed upon topical administration of this solution was lower as compared to the ophthalmic solution which contained N-lauroyl sarcosine sodium, an acylated amino acid. The detailed bioavailability study and results are described in Example 7.

In case of comparative examples 2 and 3, when the ophthalmic solutions were subjected to preservative effectiveness testing (PET), it was found that these solutions did not comply with requirement in that the "log reduction in fungi" was less than 1 log reduction when tested at day 14.

The invention claimed is:

1. An ophthalmic solution comprising
   (i) bimatoprost or its pharmaceutically acceptable salt in an amount of about 0.01% weight by volume;
   (ii) polyhexamethylene biguanide in an amount of about 0.005% weight by volume;
   (iii) N-lauroyl sarcosine sodium in an amount of about 0.03% weight by volume;
   (iv) pharmaceutically acceptable excipients; and
   (v) purified water;
   wherein the ophthalmic solution is free of benzalkonium chloride.

* * * * *